United States Patent [19]

Hedengren et al.

[11] Patent Number: 5,262,722
[45] Date of Patent: Nov. 16, 1993

[54] APPARATUS FOR NEAR SURFACE NONDESTRUCTIVE EDDY CURRENT SCANNING OF A CONDUCTIVE PART USING A MULTI-LAYER EDDY CURRENT PROBE ARRAY

[75] Inventors: Kristina H. V. Hedengren; Richard J. Charles, both of Schenectady; William P. Kornrumpf, Albany, all of N.Y.

[73] Assignee: General Electric Company, Schenectady, N.Y.

[21] Appl. No.: 862,699

[22] Filed: Apr. 3, 1992

[51] Int. Cl.[5] .................... G01N 27/90; G01R 33/12
[52] U.S. Cl. .................................. 324/242; 324/262; 336/200
[58] Field of Search ................ 324/234, 236, 237–243, 324/260–262; 336/20, 200, 206

[56] References Cited

U.S. PATENT DOCUMENTS

| | | | |
|---|---|---|---|
| 4,547,962 | 10/1985 | de Walle et al. | 324/262 X |
| 4,593,245 | 6/1986 | Viertl et al. | 324/238 |
| 4,706,020 | 11/1987 | Viertl et al. | 324/262 |
| 4,706,021 | 11/1987 | Chamuel | 324/242 |
| 4,990,851 | 2/1991 | Spies | 324/240 |
| 5,047,719 | 9/1991 | Johnson et al. | 324/242 |

OTHER PUBLICATIONS

"Eddy Current Printed Circuit Probe Array: Phase I," T. G. Kincaid, Signametrics Report No. 9, Sep. 12, 1987 (also appeared as an appendix to a GE final report).
"Eddy Current Printed Circuit Probe Array: Phase IIA," T. G. Kincaid, Signametrics Report No. 10, Dec. 29, 1988 (also appearing in a GE Final Report No. 2880582Y20XG, "Eddy Current Technology Department," Jan. 1989 as an appendix).
"Flexible Substrate Eddy Current Coil Arrays," Y. D. Krampfner and D. D. Johnson, Review of Progress in Quantitative Nondestructive Evaluation, vol. 7A, pp. 471–478, 1988.

Primary Examiner—Gerard R. Strecker
Assistant Examiner—Warren S. Edmonds
Attorney, Agent, or Firm—Paul R. Webb, II

[57] ABSTRACT

An apparatus for near surface, nondestructive eddy current scanning of a conductive part using a multi-layer eddy current probe array. Such structures of this type, generally, employ an ultra-thin, flexible, film-like, multi-layer eddy current probe array which is adapted to provide routine inspection of conductive parts while also providing improved signal integrity, signal transmission and isolation.

28 Claims, 9 Drawing Sheets

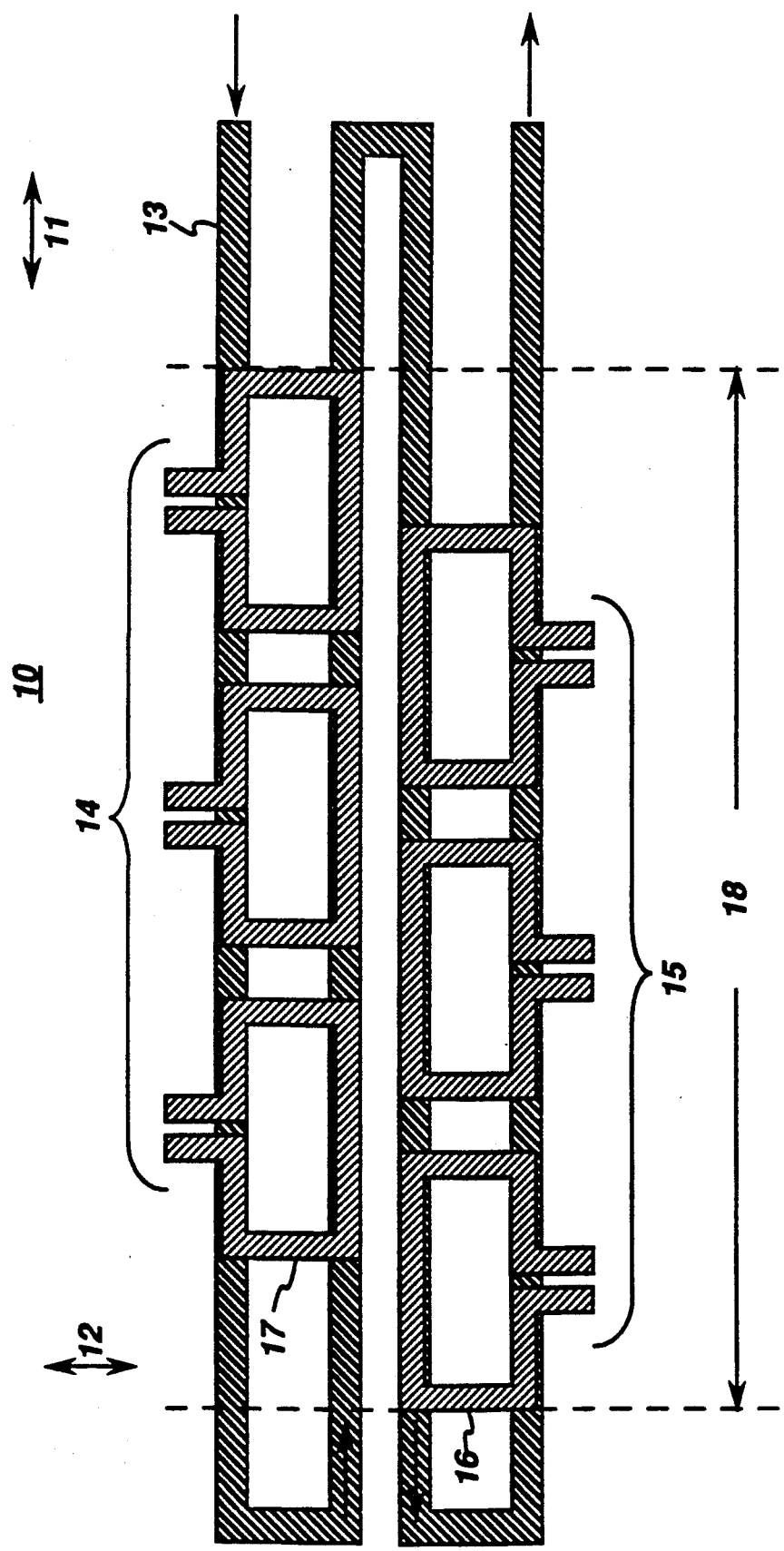

APPARATUS FOR NEAR SURFACE NONDESTRUCTIVE EDDY CURRENT SCANNING OF A CONDUCTIVE PART USING A MULTI-LAYER EDDY CURRENT PROBE ARRAY

CROSS-REFERENCE TO RELATED APPLICATIONS

The present application is related to the following commonly assigned patent applications the entire disclosure of which are hereby expressly incorporated herein by reference in their entireties:

Patent application Ser. No. 07/862,950 entitled "A DEVICE FOR INSPECTING A COMPONENT" by George H. Sutton et al, which is filed concurrently herewith describes a device for inspecting a component having complex geometry using an eddy current probe array;

Co-pending patent application Ser. No. 07/696,455 entitled "EDDY CURRENT PROBE ARRAYS" by Kristina H. Hedengren et al which discloses and claims a flexible, spatially correlated eddy current surface measurement array;

Co-pending patent application Ser. No. 07/696,456 now U.S. Pat. No. 5,182,513 entitled "METHOD AND APPARATUS FOR NONDESTRUCTIVE SURFACE FLAW DETECTION" by John D. Young et al which discloses and claims a system for acquiring a plurality of synchronized, spatially correlated, discrete eddy current measurement signals for image processing; and Co-pending patent application Ser. No. 07/504,769, now abandoned, entitled "A FLEXIBLE INTERCONNECTED SYSTEM" by Charles W. Eichelberger et al discloses and claims a high density, multi-component, multi-layer, photolithographic fabrication technology for microelements and integrated circuitry. Arrays so fabricated have precisely uniform sense elements and precise registry with respect to one another for reliably and repetitively inspecting complex geometries in an industrial environment.

FIELD OF INVENTION

This invention relates generally to apparatus for nondestructive eddy current inspection of an electrically conductive part in an industrial environment and more particularly to such an apparatus which operates in a reliable, repeatable and routine manner for inspection scanning of such a part.

BACKGROUND OF THE INVENTION

Photolithographic integrated circuit fabrication techniques have produced eddy current probe arrays having precisely uniform, miniaturized sense elements encapsulated within an ultra-thin, flexible, film-like structure for scanning conductive parts having a complex geometrical inspection surface. These flexible, film-like probe array structures are capable of closely conforming to irregular surfaces in order to inspect difficult geometries which cannot be inspected by conventional scanning means. Using High Density Interconnect (HDI) fabrication technology, probe array sense elements are encapsulated within an ultra-thin, flexible, multi-layer structure having high microcomponent density and substantial uniformity among microcomponents in accordance with application Ser. No. 07/696,455. Electrically interconnecting the multi-layer encapsulated microelements of such an eddy current probe array necessitates intra-layer connections, e.g. coplanar conductive pathways deposited onto the surface of a layer; as well as, inter-layer connections, e.g. conductor filled holes between layers operating as conductive pathways between elements disposed on different layers. These inter-layer connections are substantially normal with respect to the coplanar layers being known to those skilled in the art as "via" connections. Both types of electrical interconnections are generally encapsulated within the flexible, film-like, multi-layer structure of the probe array. Typical access to components encapsulated within the flexible, ultrathin probe array structure is accomplished by utilizing vias between coplanar conductive paths which terminate in leads either on the uppermost surface layer or the lowermost surface layer, at an edge of the flexible probe array structure. This accommodates edge oriented electrical access to typical external electrical drives, system electronics, diagnostics, physical grounds etc. Connections to the access edge of such a flexible, ultra-thin probe array structure have been necessarily customized. Array drive and sense elements must be electrically connected to an electronic data acquisition system in order to be operatively useful as an inspection system. Heretofore, the manner for making electrical connection has consisted of painstakingly hand soldering connecting wires to the individual contact pads of edge accessible leads corresponding to each encapsulated component. Such connecting wires are typically adapted to be plugged into a suitable socket type edge connector. It would be desirable, to provide a flexible, ultra-thin probe array structure with a quick and easy means for reliable electrical interconnection to conventional system electronics while ensuring reproducible rugged alignment and mounting of the film-like probe array structure in order to precisely accommodate conductive surface inspection scanning.

SUMMARY

The invention herein discloses a flexible, ultra-thin, surface conforming, film-like, multi-layer eddy current probe array structure, which is preferably fabricated by a suitable photolithographic technique. The array accommodates electrical and mechanical interconnection to respective system electronics and mechanical scanning means in order to provide improved inspection scanning of conductive parts. Improvements in the ultra-thin, flexible, multi-layer probe array structure include implementing transmission lines within the multi-layered structure to improve signal transmission to and from encapsulated array probe elements in order to enhance scan response signal integrity. Improvements further include providing adequate shielding to enhance response signal isolation. Electrically adapting a flexible, multi-layer, film-like probe array structure for durable, repeatable electrical interconnection to accommodate various standard system electronics is preferably accomplished by providing an integrally fabricated rigid connector module operating to transition and adapt precisely fabricated miniature leads from each encapsulated probe element to standardized electrical connectors for signal exchange with external electronic devices. External devices include standard image processing system electronics, external source drives, physical grounds, etc. Mechanically adapting the flexible, ultra-thin, multi-layer, film-like probe array structure for quick, easy, reproducible industrial scanning is accomplished by providing alignment and registration means integrally fabricated within the film-like structure in order to reproducibly position the probe array in cooperation with a mechanical scanner for consistent and reliable eddy current surface inspection.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings in which:

FIG. 1 is a schematic top planar view of a simplified double layer eddy current probe array;

FIG. 2b illustrates a perspective view of a system for surface inspection scanning utilizing the probe array of FIG. 2a;

DETAILED DESCRIPTION OF THE INVENTION

Figure 2A:
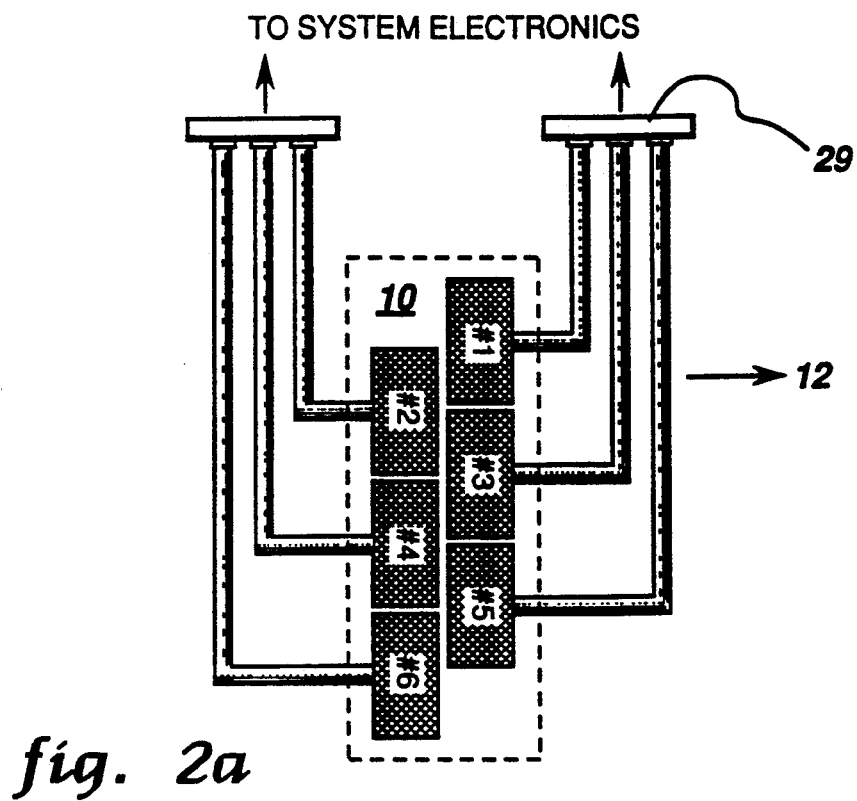
FIG. 2a illustrates a top planar view of the operational system of FIG. 1 showing electrical interconnection of probe elements to external system electronics.

FIG. 1 shows a top planar view of a simple double layer eddy current probe array 10 comprising six simple, single-turn sense coil elements configured in absolute mode and a continuous serpentine drive coil element 13 disposed in long, back and forth, parallel segments. The drive coil element 13 is shown with the instantaneous current flow direction indicated by arrows. The six sense coil elements are substantially identical single-turn coils, one of which is identified at 16.

The drive coil element 13 resides in one layer and the sense coil elements in another layer of a double layer structure as distinguished by the cross hatching of respective strips. These strips represent metallization patterns disposed in different respective layers. The probe array sense elements are staggered with respect to one another to accommodate proper scanning coverage of the inspection surface. In this design, relative staggering of adjacent rows of sense elements, as illustrated by the relative staggering of sense element 16 with respect to sense element 17, is accomplished in direction 11. Staggering establishes a preferred scanning direction 12 which is perpendicular to staggering direction 11. Staggered offsetting of adjacent rows of probe elements ensures oversampling of the inspection surface by inspection scanning in preferred direction 12; thus, eliminating nulls or blind spots which lack sensing capability. The probe array can cover a scan width given by the probe active area which is herein identified at 18. Electrical contact pads or terminal leads for making electrical connections to probe elements are generally segregated in specific locations. A preferred location is identified on either side of the array as indicated at 14, 15. For convenience and ease of connection, such electrical contacts are typically taken to the uppermost or lowermost layer of the eddy current array multi-layer structure. Probe elements are electrically interconnected to external drives, physical grounds, data channels, etc. at such contact pads or terminal leads. FIG. 1 illustrates a very simple probe array design presented for illustration purposes.

Figure 2B:
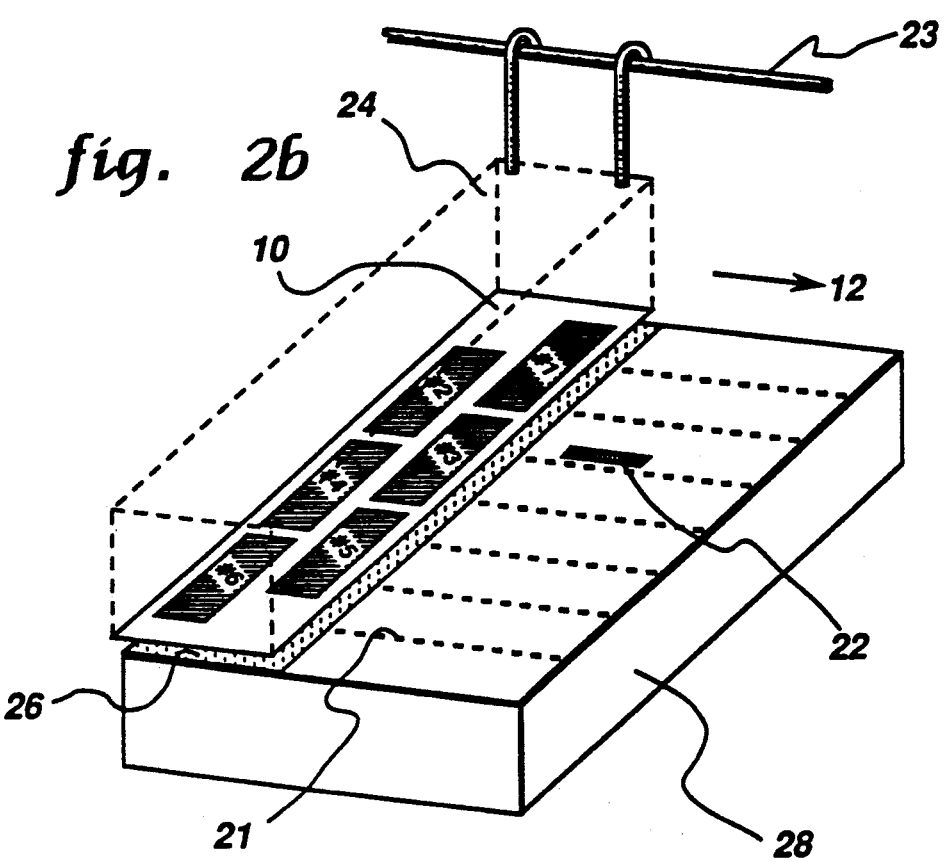

FIGS. 2a and 2b illustrate two views of a plurality of substantially identical sense elements similar in design to those of FIG. 1. FIG. 2a illustrates that each probe sense element #1-#6 of the plurality is electrically interconnected to a corresponding plurality of responsive signal output channels identified at numeral 29. Data acquisition at such output channels is described in patent application Ser. No. 07/696,456. FIG. 2b shows the same array of six sense elements disposed in a surface conforming array probe 24 which proximately disposes probe array 10 to the surface of the conductive workpiece 28 under inspection. Such near surface disposition is provided in order that each sense element #1-#6 electromagnetically couples through a correspondingly conforming underlying inspection surface 26 of conductive part 28 to at least one externally excited drive element (similar to that identified by 13 in FIG. 1). Conforming array probe 24 is slideably mounted onto slideable scanning means 23 in a precisely aligned and registered manner in order to slide across inspection surface 26 in a direction identified as preferred scan direction 12.

The scanning configuration of FIG. 2b is operated by sliding array probe 24 across the surface of conductive part 28 to accommodate inspection of underlying surface 26 while driving at least one drive element (similar to that identified by 13 in FIG. 1) with a predetermined external oscillating current source (not shown) to provide a corresponding plurality of responsive signals detected by sense elements #1-#6 for input to a corresponding plurality of data channels 29 (see FIG. 2a) for image or signal processing. Ensuring scan responsive signal integrity and isolation is crucial to transmitting the proper signal for signal processing. During row scanning the array probe 24 is indexed in only preferred direction 12. This typically involves incrementally scanning in preferred scanning direction 12 to acquire discrete scan responsive signals corresponding to signals collected at each of a plurality of discrete positions 21 along a surface conforming linear scan path. In order to inspect the entire surface of conductive part 28, array probe 24 can be used to scan across the entire inspection surface in one unidirectional scan, so long as the surface under inspection can be covered by an array scan width as identified by the width of the array's active area (see numeral 18 of FIG. 1). If the surface under inspection cannot be covered by an array scan width, the surface can be scanned repeatedly in a stripwise fashion preferably in the same direction. In either case, incremental scanning involves scanning to cover a conforming scan width strip (identified by numeral 18 in FIG. 1) of the conductor surface so as to cover the entire conductor surface in a predetermined number of stripwise scans. Clearly probe array mounting and alignment are crucial to providing complete coupling coverage using a repeated interval scanning procedure.

In operation, the two staggered rows of sense elements, as illustrated in FIG. 2a, provide overlapping scan coverage of inspection surface 26. Sense elements are disposed in rows across the surface of conductor 28 in a direction oriented perpendicular to scan direction 12. Staggering provides complete scanning surface coverage due to overlapping. Furthermore, staggering provides responsive signals, generated from each sense element of the plurality, that selectively oversample the inspect surface by scanning in preferred scan direction 12. Thus, by assuring complete scanning coverage of the underlying inspection surface 26, inspection thereof can be accomplished in a single unidirectional scan. Overlapping and resultant surface oversampling by scan responsive signals eliminate unwanted "blind spots" that may otherwise exist between non-overlapping array sense elements. Staggered overlapping ensures that near surface flaw 22 will be detected. In addition, overlapping provides redundant detection signals of flaw 22 in scan responsive signals of both sense element #2 and sense element #3. This redundancy provides a corresponding simultaneous enhancement in signal sensitivity and resolution capability. Probe array 10 illustrated in the embodiment of FIGS. 1, 2a and 2b is shown conforming to a flat inspection surface. The availability of flexible probe arrays, such as those described in patent application Ser. No. 07/696,455, also accommodate conformable surface scanning of non-planar geometries. Such complex curved surface scanning of a surface preferentially having translational symmetry can be accomplished in one unidirectional scan along the axis of translation using a suitably adapted array probe. If the surface to be inspected does not exhibit an axis of translation, repeated stripwise scanning of an active array width portion of the surface can effectuate inspection with substantially equivalent reliability so long as accurate and reproducible alignment and registry of the probe array with respect to the inspection surface is ensured.

Figure 3:
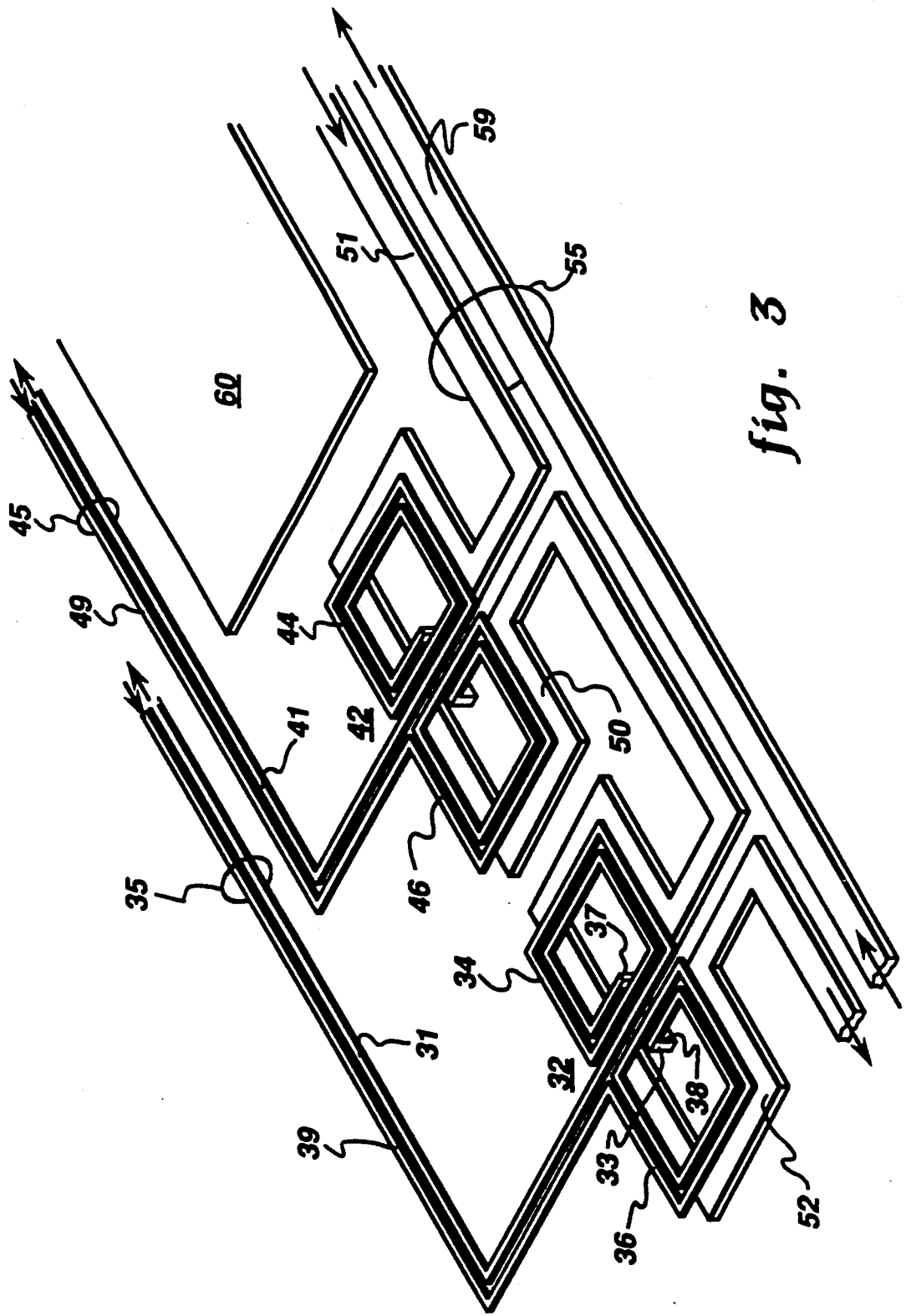
FIG. 3 is a schematic perspective view of a portion of a double layer eddy current probe array film-like structure illustrating two sense coils and a drive coil in accordance with the invention.

FIG. 3 illustrates an enlarged schematic, dimensional, view of one embodiment of an eddy current probe array film-like structure illustrating two, double turn, double-layer coils 34, 36 configured in differential mode comprising sense coil element 32. Sense coil element 42 is similarly comprised of coils 44 and 46. Sense elements 32 and 42 are respectively coupled to underlying single loop drive coils 52 and 50 These coil elements are preferably fabricated using a multi-layer photolithographic technique similar to GE's High Density Interconnect (HDI) technology as described in accordance with patent application Ser. No. 07/696,455. Sense element 32 illustrates two, double turn, double layer coil elements connected in differential mode; wherein, conductive segment 38 is disposed in a layer other than the layer in which turns 34, 36 of coil element 32 reside. For identical coil elements, this type of connection provides a "virtual ground" operating as a common reference potential for identically induced coil voltages. Providing a virtual ground for coil elements connected in differential mode eliminates the need to provide a physical ground connection. Interlayer metallization using "via" connections at 33 and 37 divert the conduction of electricity through the coils to another layer through conductive segment 38 in another layer. Vias are used to make electrical connection between the terminating contact pads of elements in different layers of a multi-layer probe array film-like structure in accordance with copending patent application Ser. No. 07/696,455. In the configuration of FIG. 3, both double turns 34, 36 of sense element 32 reside in the same layer. Drive coils 50, 52 reside in a layer different from that of the sense element turns. Arrows indicate the respective instantaneous direction of current flow at respective sense and drive leads. Electrical connections to, from, and between such elements and other integrated components, external sources, grounds, and I/O ports are accomplished using appropriate inter-layer via connections and appropriately designed conductive segment pathways. These conductive segment pathways are preferably linear, operating to carry intra-layer electrical signals to and from elements within the same layer. Vias are typically used to make inter-layer electrical connections eventually directing signals toward the edge of a multi-layer film-like probe array structure at either its uppermost or lowermost layer. Leads from sense elements e.g. 32, 42 and drive elements e.g. 50, 52 are preferably designed to form pairs of parallel linear conductive segment pathways 35, 45, 55 respectively which operate as independent miniature transmission lines in accordance with the invention. Sense element pair 35 is comprised of sense leads 31 and 39. Sense element lead pair 45 is comprised of sense leads 41 and 49. Drive element lead pair 55 is comprised of drive leads 51 and 59. Layout design is adapted, preferably by computer, to fully utilize the benefits of transmission line configurations. Furthermore, lead dimension are preferably adapted to normalize signal impedance. Depending on the materials utilized, benefits derived from using transmission line signal conduction mode include: transmission of high fidelity signals, reduction of unwanted cross-coupling, etc. Therefore, designing a probe array structure to emulate transmission line behavior improves signal integrity in accordance with the invention. Another specific benefit suggested by treating signal conductive pathways pairs as independent transmission lines is derived from utilizing a shielding feature, e.g. 60 integrally fabricated with the eddy current probe array film-like structure. Internal shielding is conceptually treated in much the same way as conventional cable shielding. However, shielding is herein provided in a flexible, integrated, multi-layer structure preferably fabricated by photo-lithographic techniques by depositing metallization strips, e.g. 60, of suitable conductor between conductive transmission line pair pathways that are likely to experience unwanted coupling. Signal to noise ratios are increased and detection capability is improved by introducing shielding strips, e.g. 60, between drive lead pairs e.g. 55 and sense lead pairs e.g. 45. These strips, e.g. 60, are preferably wider than the conductive pathway strips that comprise the leads themselves e.g. 31, 39, 41, 49, 51, 59. The shielding provided by selective metallization strip 60 improves signal isolation, signal integrity and signal sensitivity in accordance with the invention. Flexible, multi-layer, integrated probe array film-like structures fabricated by photolithographic techniques are thereby improved by enhancing signal integrity as well as signal isolation.

Figure 4:
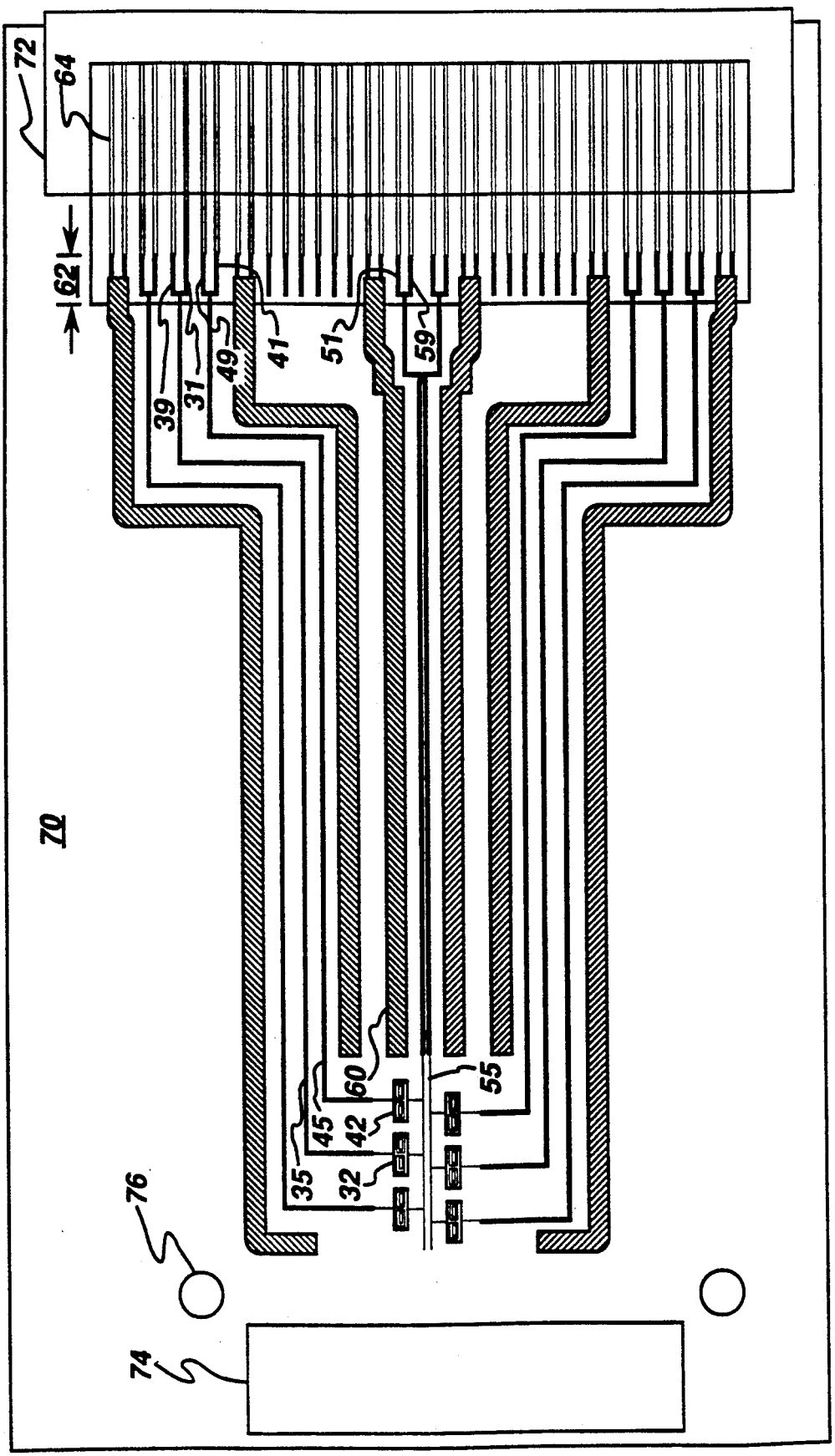
FIG. 4 is a schematic top planar view of a probe array with two staggered rows of three elements each, similar to those illustrated in of FIG. 3, indicating the preferred embodiment of the present invention.

FIG. 4 is a schematic illustration of a top planar view of a six coil element probe array filmlike structure 70 of double layer design similar to that of FIG. 3. Sense elements 32 and 42 are indicated. As this is a top planar view, the underlying drive element 52 is not visible in FIG. 4. Sense element transmission line lead pairs are indicated at 35 and 45; while a drive element transmission line lead pair is identified at 55. One of many such shielding strips is identified at 60. Each transmission line lead becomes dissociated into a corresponding lead pair. For example, transmission line sense lead pair 35 dissociates into individual leads 31 and 39. FIG. 4 illustrates similar dissociation of leads 41 and 49 from transmission line sense lead pair 45. Likewise, transmission line drive lead pair 55 dissociates into individual leads 51 and 59. This dissociation into individual leads is generally accomplished in region 62 proximate to the edge of connector module 72. Each dissociated lead pair appears as a uni-layer lead pair "fork" which is transitioned into corresponding finger-like metallization strips, e.g. 64, being deposited onto rigid, non-conducting connector module 72. FIG. 4 illustrates the disposition of lead pairs 35, 45, 55 in parallel, linear segments cooperating as transmission lines transmit signals to edge region 62 in order to make connection to other electronics using a suitable commercial edge connector (not shown) by way of connector module 72. FIG. 4 also illustrates the disposition of shielding strips, e.g. 60, to isolate drive lead pair signals from sense lead pair signals. Shielding isolates these respective signals from extraneous coupling as well. FIG. 4 further illustrates the use of a rigid, non-conductive connector module 72 having a plurality of precisely disposed, uniform finger-like metallization strips, e.g., 64, disposed in a manner to accommodate coupling to a standardized commercial edge connector (not shown). In addition, FIG. 4 illustrates representative fabrication of a registration block 74 and alignment apparatus 76 for mechanically aligning and registering the probe array structure 70 into a mechanical scanning means (not shown).

Figure 5:
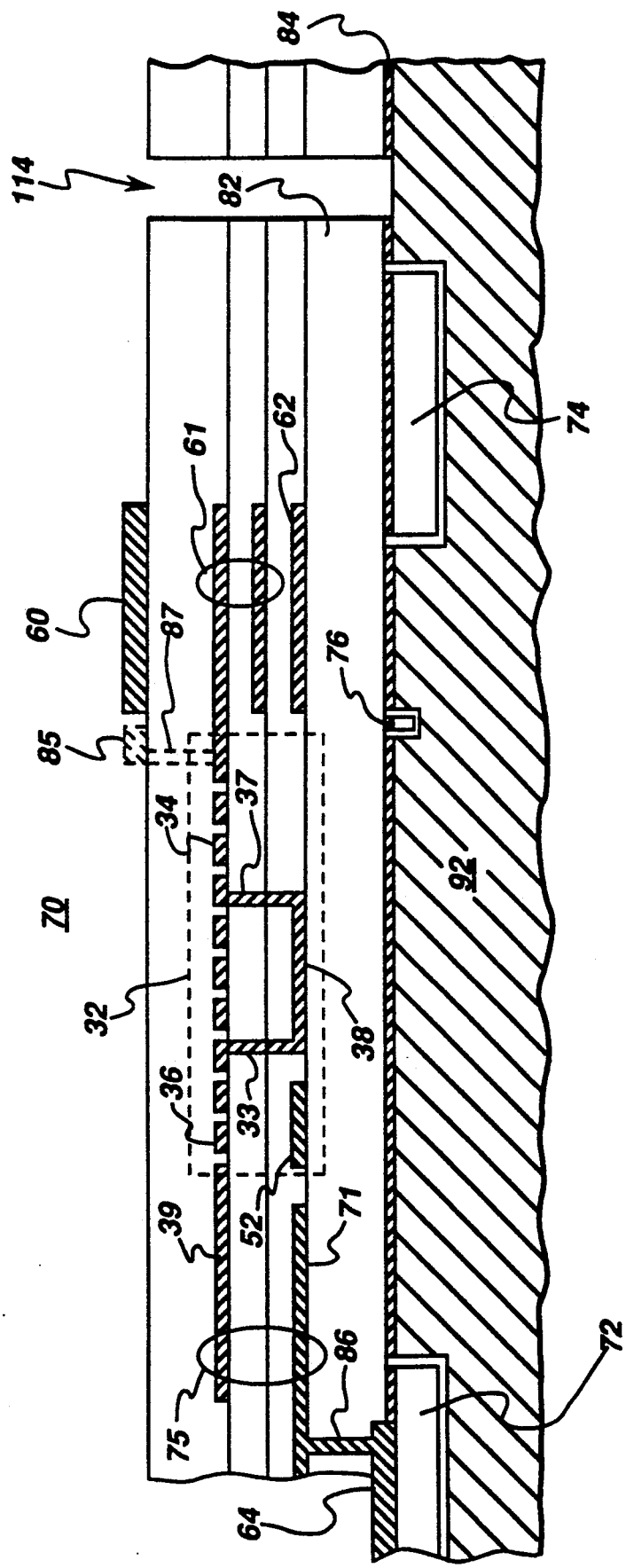
FIG. 5 is a planar, cross-sectional conceptual view through a representative probe array film-like structure illustrating novel features indicated in FIGS. 3 and 4.

FIG. 5 illustrates a planar, cross-sectional view through the probe array structure 70 without showing the detail of component cooperation shown in FIGS. 3 and 4. FIG. 5 is a conceptual view which representatively illustrates, in greater detail, novel features of probe array film-like structure 70 which are shown in cross section in accordance with the invention. These novel features include: probe element lead pairs cooperating as transmission lines to conduct responsive signals to and from probe elements; shielding strips disposed to isolate such responsive signals; connector module; alignment means; and registration block. Although; in actuality, no single slice through a multi-layer probe array film-like structure is likely to reveal all the novel elements identified and discussed in FIGS. 3 and 4; these elements are representatively illustrated in the same cross sectional planar slice in FIG. 5 only for the sake of discussing these collective features.

FIG. 5 illustrates a transmission line 75 formed by a lead pair comprised of leads 71 and 39 from sense element 32 (shown in dotted lines). Each transmission line is fabricated as a pair of respective probe element (sense or drive) leads. The respective lead pair can be disposed in the same layer or in different layers. Probe lead pairs disposed in the same layer are indicated at 35, 45, and 55 in FIG. 3 comprising unilaminar transmission lines; but, do not lend themselves to cross-sectional illustration. Leads 71, 39 of FIG. 5 have been fabricated in different layers of a multi-layer probe array film-like structure as metallization strips and cooperate as strip transmission line 75. Transmission lines accommodate uniform signal having low loss due to decreased coupling between lead pairs.

FIG. 5 also illustrates shielding strips 60 and 62 deposited between sense and drive transmission line lead pairs in the same or different layers. Shielding strip 60 in FIG. 3 is deposited in the uppermost layer between sense transmission line pairs 35, 45 and drive transmission line pair 55. Shielding strips 60 and 62 are disposed as metallization strips deposited on different respective dielectric layers of multi-layer probe array film-like structure 70. Shielding strips operate to isolate probe element lead pairs from extraneous coupling sources thereby isolating responsive signals carried thereon. Same layer shielding interposes a metallization strip, e.g. 60, preferably wider than those metallization strips which operate as probe element leads, e.g. 35, 45, and 55, in the same layer between sense and drive lead pairs to horizontally isolate the signal carried thereby from extraneous coupling as shown in FIG. 3. Similarly, shielding between different layers is accomplished by interposing metallization strips, e.g. 60, 62, preferably wider than those metallization strips operating as probe lead pairs 61 between layers wherein probe lead pairs reside in order to vertically isolate the signals carried thereby from extraneous coupling.

FIG. 5 also illustrates a multi-layer probe array film-like structure having integrally fabricated connector module 72, registration block 74, and alignment means 76. Detail of the dissociation of each transmission line pair formed by sense or drive element lead pairs into individual leads corresponding to each respective element has already been discussed and identified in FIG. 3. Note that each lead must first be isolated to accommodate individual electrical connection to an appropriate external device e.g. oscillating current source, input-/output device, physical ground, etc. To facilitate individual electrical connection of each respective lead, a novel connector module is implemented in accordance with one embodiment of this invention. Connector module 72 is fabricated as an integral part of the probe array film-like structure preferably using a photolithographic process, e.g. HDI technology. A probe array film-like structure is fabricated by initially bonding a flexible wear resistant substrate 82, such as Kapton TM, a polyimide film available from E.I. DuPont de Nemours Company, to a rigid support carrier 92, typically made of Kovar TM steel, to support the flexible substrate 82 throughout photolithographic processing. Such support is required in order to avoid shrinking, wrinkling, etc. Substrate 82 could also be a flexible or rigid ferrite material. Substrate 82 is adhesively adhered to support carrier 92 by pretreating support carrier 92 with a thermoplastic adhesive 84 such as Ultem TM, a polyetherimide available from the General Electric Company. Select cavities are cut using laser or EDM (Electro-Discharge Machining) techniques into support carrier 92 in order to insert a rigid nonconductive base for fabricating connector module 72, registration block 74 and alignment means 76 therein; said items being flush with the surface of support carrier 92. A metallization process such as sputtering or electroplating is used to apply metallization strips or "fingers" e.g. 64 to connector module 72 before application of substrate 82. Fingers are patterned using photoresist then the metallization pattern is exposed and etched away using a suitable etchant to pattern the fingers. Metal fingers e.g. 64 are preferably made of an inert, low resistance metal like gold and deposited onto connector module 72 which is preferably made of a rigid, nonconducting material, such as ceramic. The ceramic material rigidly supports gold electrical leads ('gold fingers'). Metal strip fingers can be patterned onto one or both sides of rigid connector module 72, depending upon whether single-sided or double-sided electrical coupling to a commercial connector is desired. FIG. 5 illustrates only one sided deposition of finger-like strips onto connector module 72 although double-sided deposition can be similarly accomplished. Laser ablation is used after completion of the probe array structure fabrication process to carve away multi-layer deposits so that gold finger-like leads 64 are exposed for electrical interconnection. Connector module 72 provides means for precisely spacing gold finger leads onto a durable, rigid, non-conductive, inert support structure to facilitate rugged, reproducible electrical interconnection of an otherwise flexible, ultra-thin eddy current probe array film-like structure into a commercially available edge connector (not shown in FIG. 5). Connector module 72 accommodates electrical connections to unilaminar leads originating at probe elements e.g. 32 encapsulated within various layers of multi-layer probe array film-like structure 70. Directing leads to a single layer is accomplished by via connections through respective layers of the multi-layer structure. Via 86 is illustrative of many such via connections required to direct leads originating from respective probe elements e.g. 32 to connector module 72 . Vias 87 can alternatively be utilized to provide electrical connection from an element e.g. 32 encapsulated in the probe array film-like structure to an upper surface contact pad e.g. 85 on the surface of the film-like structure 70. Surface contact pad e.g. 85 can be utilized to make direct electrical interconnection to contact pads of external electronic devices rather than utilizing a connector module 72 having finger-like leads 64 for making indirect electrical interconnection.

Connector module 72 is utilized to accommodate interconnecting leads to standard edge connectors; wherein, connector module 72 can accommodate several types of commercially available connectors. Several commercial connectors which accommodate high density electrical interconnection include: a Betaflex ™ multi-row, micro-strip, pressure loaded edge connector; a pressure deformable elastomeric connector such as the Fujipoly ™ W Series or Elastomeric Technologies Inc.(ETI ™) Matrix MOE ™ elastomeric connector; a Nanonics ™ Nanominiaturer ™ single row strip or Dualobe ™ spring socket connector; etc. Some commercial connectors can accommodate a connector module having double-sided finger-like contacts while others cannot. In accordance with the invention, fabrication of connector module 72 can be adapted to each customized application by virtue of the commercial connector chosen for that application.

Figure 6:
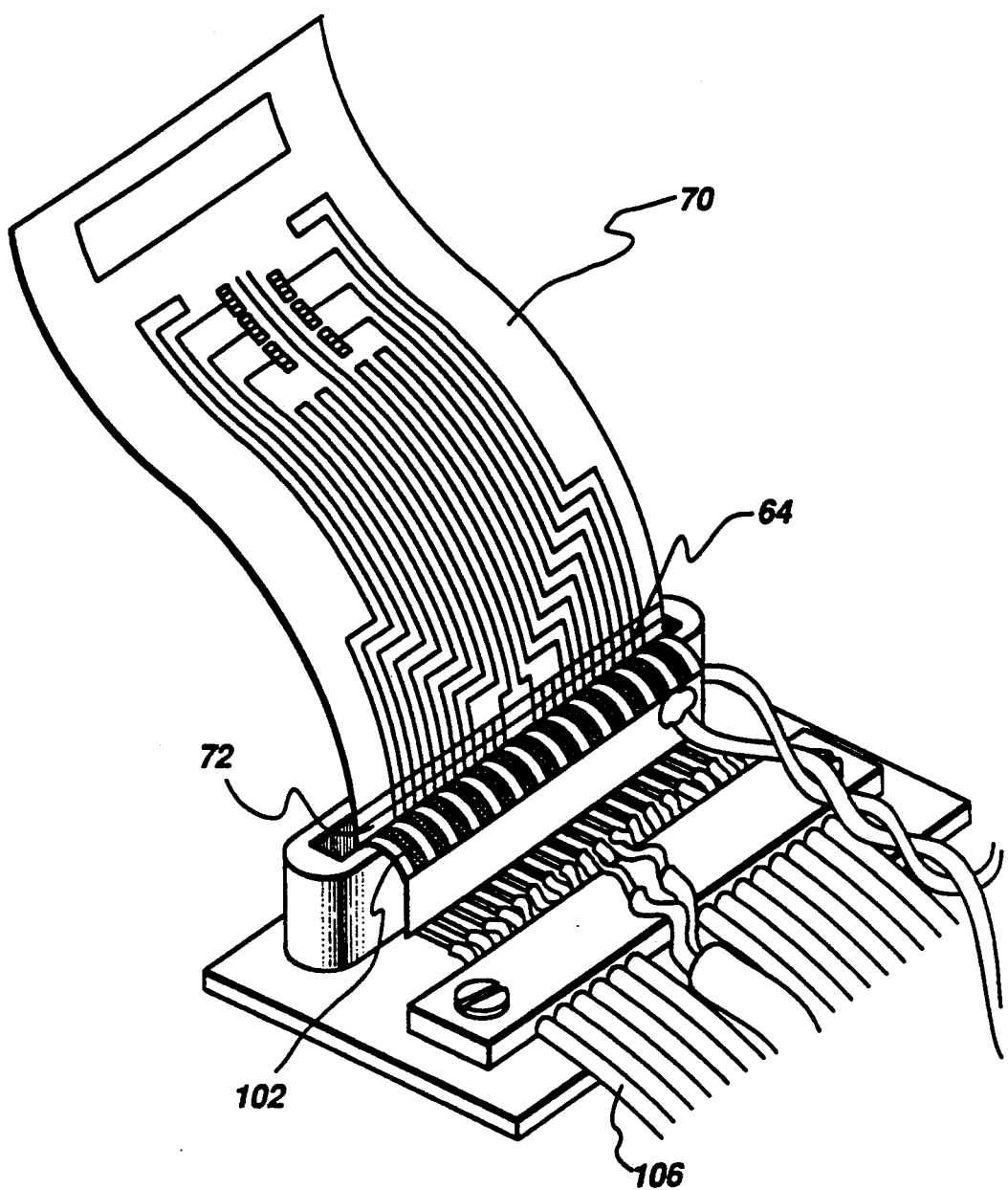
FIG. 6 is a schematic view of an embodiment of a probe array film-like structure having a rigid, integral connector module for accomplishing electrical interconnection to a pressure loaded edge connector.

FIG. 6 illustrates one embodiment of the invention wherein a rigid, non-conducting connector module 72 is fabricated as an integral part of probe array film-like structure 70 and makes electrical connection to a commercial connector 102 like the Betaflex multi-row, micro-strip pressure loaded edge connector, to provide electrical interconnection to drive and sense electronics through a matrix of leads 106. As previously mentioned, a similar edge connector could be utilized to accommodate a connector module having finger-like contact leads deposited on both sides of the connector module 72.

Figure 7A:
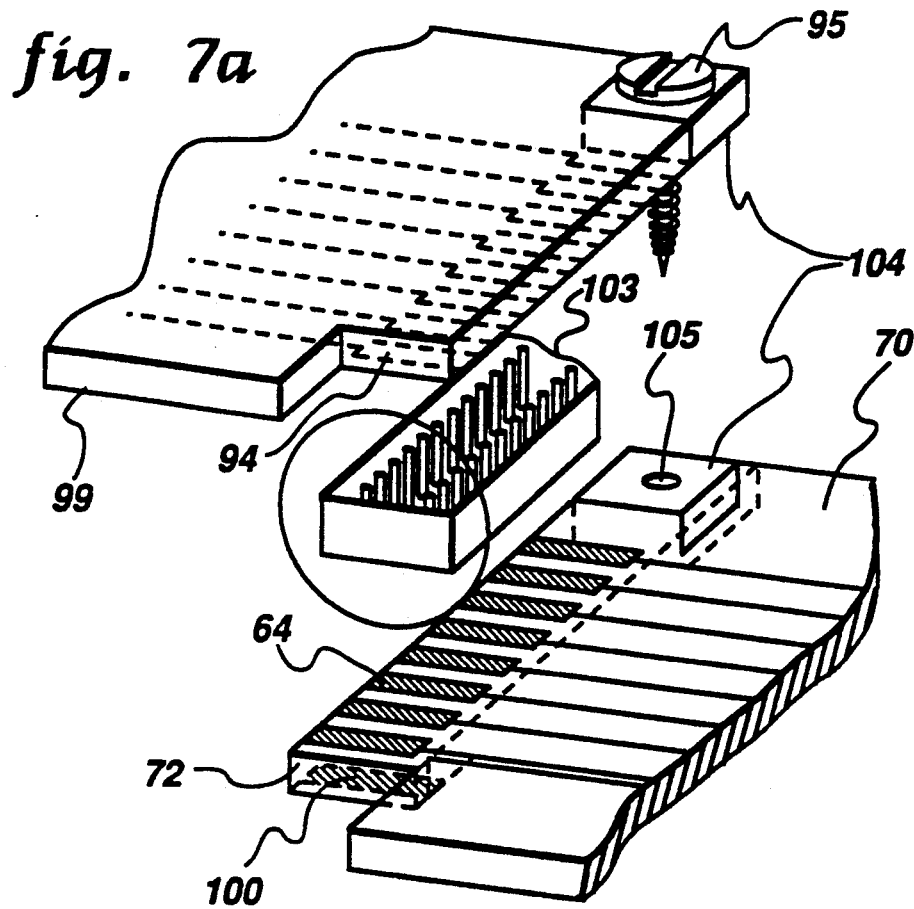
FIGS. 7a and 7b are exploded views of a schematically illustrated pressure deformable elastomeric connector shown positioned for making respective electrical connection between leads of a standardized circuit board and leads of the integral connector module of a probe array film-like structure.
Figure 7B:
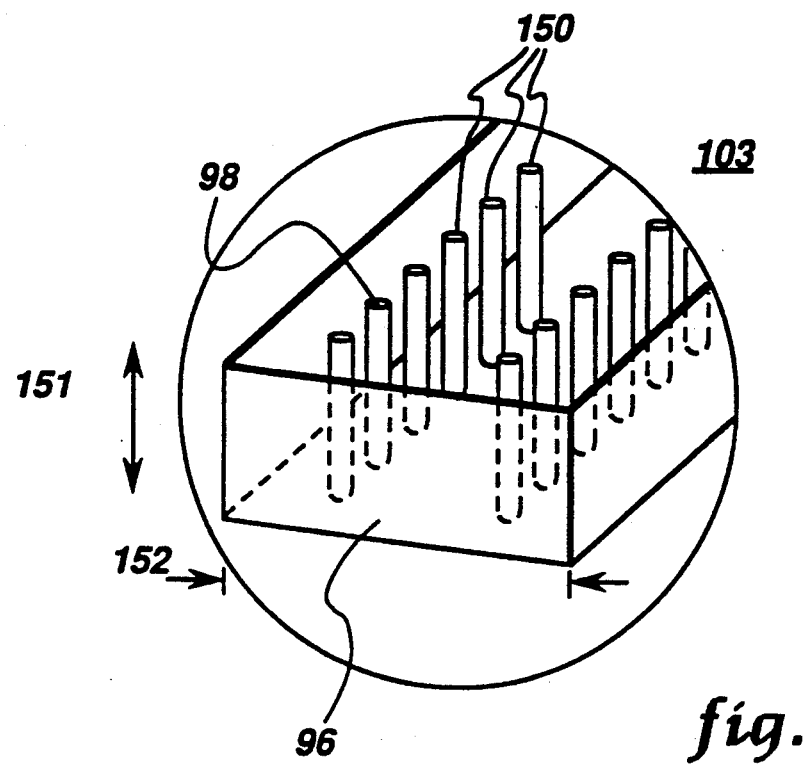

Another embodiment utilizing connector module 72 is illustrated in FIG. 7a for use with various elastomeric connectors such as the Fugipoly W series or the ETI Matrix MOE. An elastomeric connector 103 is shown in exploded view in FIG. 7b to be generally made of an nonconductive, elastomeric substrate 96, such as silicone rubber, having a dense plurality of highly conductive matrix elements 98 disposed on the surface of substrate 96 and extending through substrate 96. A matrix of leads 150 comprise a plurality of conductive matrix elements 98 operating to provide an elastomeric connector having anisotropic conductivity whereby the electrical conductivity is high in its thickness dimension 151 and low in its laminar dimension 152. FIG. 7a shows electrical connection between external electronic device 99, such as a printed circuit board, and connector module 72 is accomplished by inserting elastomeric connector 103 between printed circuit board 99 and connector module 72 and applying appropriate surface pressure using a suitable clamping means 104 to deform the elastomeric substrate 96 causing the conductive matrix elements 98 to make electrical contact between finger-like metallization strips e.g. 64 of connector module 72 and electrical contact surfaces e.g. 94 of external electronic device 99. To accommodate this, connector module 72 is preferably fabricated with at least one registration hole 105 for mechanical surface coupling to external electrical device 99 using a corresponding mating pin or screw 95. FIG. 7a illustrates that connector module 72 can be fabricated with finger-like contacts e.g. 64, 100 on either side of connector module 72 to accommodate double-sided electrical connections. Such double sided connection capability accommodates similar connection of yet another external circuit board (not shown) to the other side of connector module 72 thereby fully utilizing the available interconnect density. Alternatively, double sided connection capability could accommodate various commercial double sided connectors.

Figure 8:
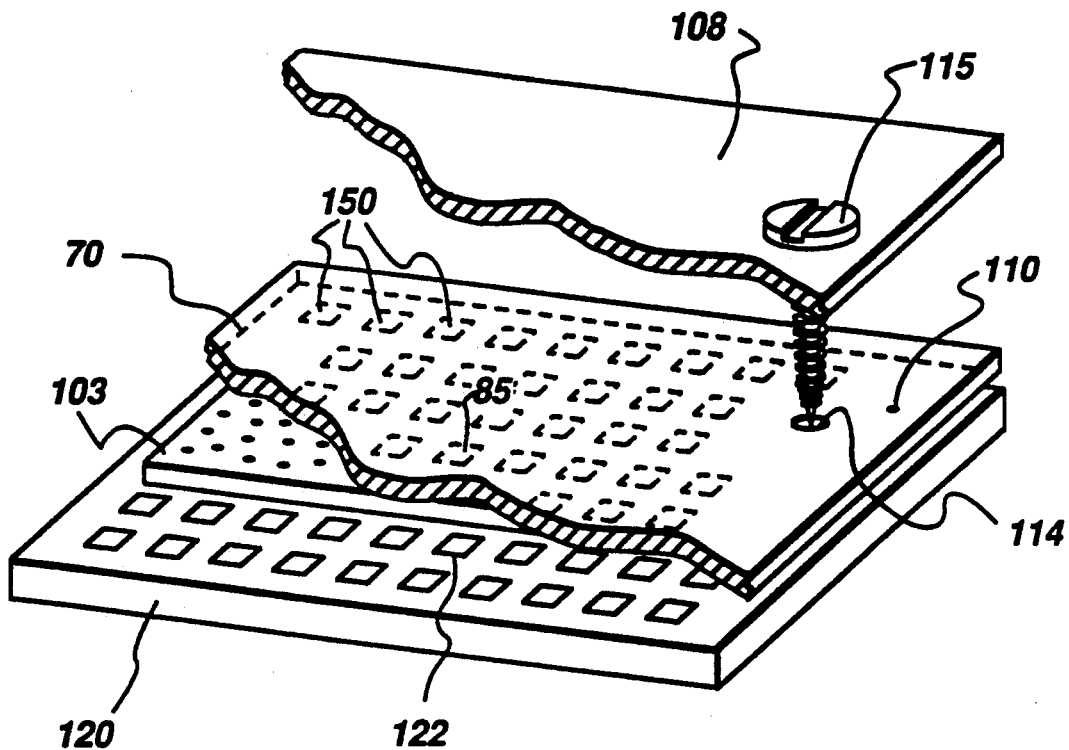
FIG. 8 is a cut away expanded view of a similar elastomeric connector positioned for making electrical connection between surface contact pads of a standardized circuit board and surface contact pads of a probe array film-like structure itself.

In still another embodiment illustrated in FIG. 8, similar elastomeric connector 103 can be utilized directly with probe array film-like structure 70 without need of connector module 72. In order to accomplish this, contact pads e.g. 85 (as seen in FIG. 5) can be fabricated so as to be precisely disposed upon the surface of flexible probe array film-like structure 70 in respective alignment with alignment hole 114 on the surface of probe array film-like structure 70. Alignment hole 114 provides registry to precisely align a plurality 150 of contact pads 85 with respect to mechanical registration means during connection of array film-like structure 70 to external electronic device 120. These contact pads 85 are electrically connected to the flexible array transmission lines by vias e.g. 87 as shown in FIG. 5. All of the electrical connections (drive elements, sense elements, and shields) are brought to the upper surface of probe array film-like structure 70 for selective connection through an aligned matrix 150 of respective contact pads e.g. 85 so as to make electrical contact with external electronic device 120 through respective contact pads e.g. 122. The use of a two dimensional contact matrix 150 greatly increases the interconnect density achievable in any given area. Mechanical registration and coupling means, include at least one alignment hole e.g. 114 and corresponding mating pin or screw e.g. 115. Each alignment hole 114 is disposed precisely with respect to flexible probe array film-like structure surface contact pad matrix 150 and operates to securely position each contact pad 85 with respect to a corresponding contact pad 122 of external electronic device 120 using corresponding mating pin or screw e.g. 115. To provide necessary mechanical stability, probe array film-like structure 70 is preferably laminated onto a suitably stiff substrate 108. Proper alignment must be insured to provide proper electrical contact between respective contact pads (e.g. 85 and 122) after surface pressure is applied to the elastomeric connector 103 using suitable clamping means herein provided by mechanical coupling of alignment hole 114 with mating pin or screw 115.

The above embodiments utilize elastomeric connectors; however, it is within the scope of the present invention that other anisotropic conductors might alternatively be utilized in place of commercially available elastomeric connectors.

Figure 9:
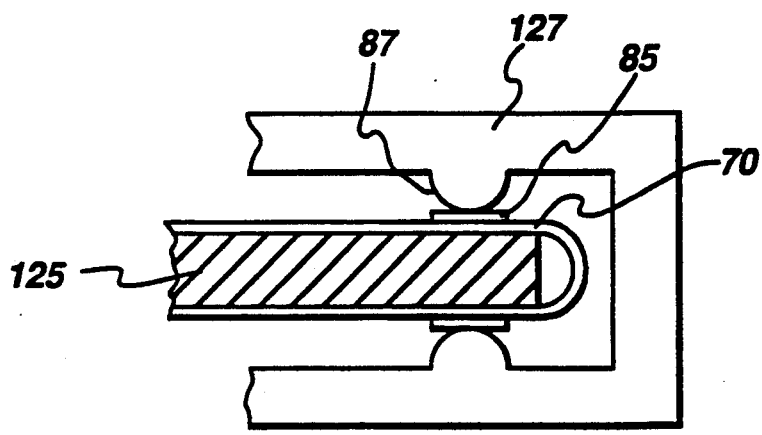
FIG. 9 is a cross sectional view through another embodiment of the invention wherein a rigidly supported probe array film-like structure is lapped over and inserted directly into a pressure loaded edge connector.

In yet another embodiment of the invention illustrated in FIG. 9, electrical connection to external electronic devices is accomplished by affixing probe array film-like structure 70 directly onto a suitable non-conducting, stiffening substrate 125 wherein probe array film-like structure 70 can be resiliently lapped over rigid substrate 125 and directly inserted into a suitable pressure loaded edge connector 127 having single or double sided contact leads similar to a Betaflex. The edge connector contacts e.g. 87 make respective contact with contact pads e.g. 85 to operably connect the encapsulated probe array elements as shown in FIG. 5. Such adaptations are within the scope of applicants' invention.

Figure 10:
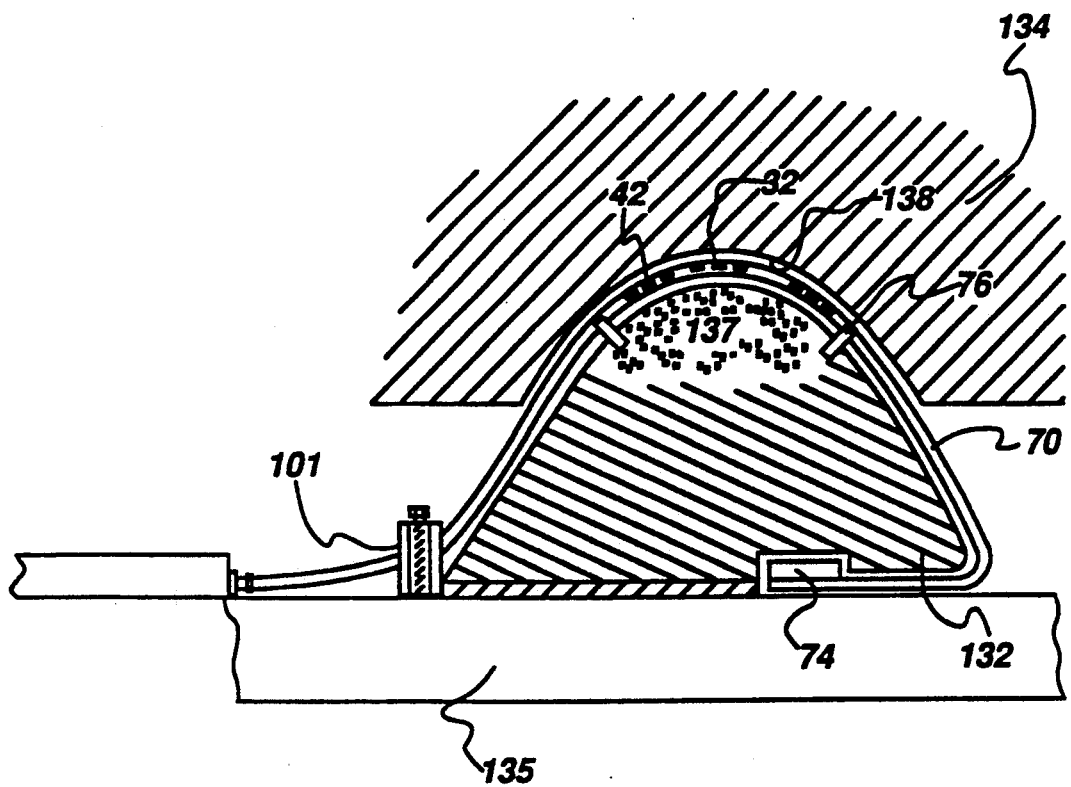
FIG. 10 is a cross sectional view illustrating precision registry and alignment of a probe array film-like structure onto a mechanical scanner for reproducible routine scanning in accordance with the invention.

Yet another embodiment of applicant's invention is illustrated in FIG. 10. FIG. 10 illustrates a mechanism for affixing, by suitable mechanical attachment, probe array film-like structure 70 onto a rigid inspection scanning support shape 132 whose scanning surface shape is the conformed mated complement of inspection surface 138 in order to accommodate conformal mechanical scanning of this complex geometrical surface of inspection part 134 using a suitable scanning means (see 23, 24 of FIG. 2b). Surface conforming support shape 132 is rigidly mounted to actuating structure 135 which cooperates together with suitable scanning means to operate as a slideable array probe (indicated by numeral 23, 24 in FIG. 2b). Scanning relies upon proper registry and alignment to ensure precise, reproducible proximal disposition of sense elements of the surface conforming array 70 with respect to the underlying inspection surface 138 during each inspection scan cycle. Note scanning takes place in a direction perpendicular to the plane of FIG. 10. Registration of probe array film-like structure 70 with respect to rigid support structure 132 is required so that accurate information is provided about the location of any near surface defect (see 22 of FIG. 2b) detected during scanning of inspection surface 138 of conductive inspection part 134. Surface alignment means can include a registration block 74 or at least one mating pin 76 coupled into at least one corresponding hole, to aid in precisely aligning flexible probe array film-like structure 70 within the scanning means. Precise surface alignment is accomplished by anchoring probe array film-like structure 70 against scanning support structure 132 with registration block 74, then stretching film-like structure 70 about the scanning support structure and precisely locking it into position for scanning using mating pin 76 and a corresponding insertion hole. This is done so that sense elements e.g. 32, 42 are precisely positioned for scanning inspection surface 138 of inspection part 134 preferably with ferrite material 137 backing the active area (see 18 of FIG. 1) of probe array film-like structure 70. Stretched probe array film-like structure 70 is fastened to mounting structure 135 using at least one selectively disposed attachment means 101 herein illustrated by a locking pin arrangement. In addition to such attachment means 101, a registry block 74 cooperates to reliably and reproducibly mate with a complementary registration hole in scanning support structure 132 to register probe array film-like structure 70 for scanning conforming inspection surface 138. Alignment element 76, e.g. at least one mating pin, couples to at least one select insertion hole in order to accommodate precise alignment of the active area of probe array film-like structure 70 for reproducible scanning of inspection surface 138 to detect near surface flaws and defects. In this manner scanning is conducted in a rugged, reliable, repetitive manner, as registry and alignment are imposed in a quick and easy manner for each scanning cycle. Thus, a reproducible alignment and registry capability is integrally embodied in the flexible multi-layer probe array structure itself to ensure scan responsive signal reproducibility.

In accordance with the invention, not only has signal reproducibility been assured due to mechanical alignment and registry of a flexible, ultra-thin eddy current probe array film-like structure in a suitable mechanical scanning device; but signal transmission quality within the array itself has been enhanced through improvements to the array. Enhanced signal quality in flexible, multi-layer eddy current array structures fabricated by photolithographic techniques has been achieved by implementing transmission lines and using suitable shielding to ensure signal fidelity and reduce cross-coupling among independent signals. Photolithographic processing offers computerized control of probe array interconnection design in order to limit undue signal loss and unwanted cross-coupling; thus, providing improved scan responsive signal integrity and isolation. Means to aid alignment and mounting as well as providing electrical connections to and from the flexible eddy current probe array structure serve to improve probe array structures to better accommodate routine industrial scanning inspection applications employing conventional electronics.

While specific embodiments of the invention have been illustrated and described herein, it is realized that numerous modification and changes will occur to those skilled in the art. It is therefore understood that the appended claims are intended to cover all modification and changes as fall within the true spirit and scope of the invention.

What is claimed is:

1. Apparatus for near surface inspection scanning of an electrically conductive part comprising:
   an eddy current probe array having a plurality of probe elements further comprising substantially identical eddy current sense elements and at least one drive element operatively connected to said sense elements such that said sense elements and said drive elements are disposed within a flexible, multi-layer, dielectric structure wherein said at least one drive element is electrically interconnected to at least one external alternating current source, said plurality of sense elements are mutually coupled to said at least one drive element through an inspection surface during scanning of said part, and said a plurality of sense elements are electrically interconnected to a select plurality of output channels in order to operatively collect scan responsive signals therefrom;
   a plurality of conductive pathways substantially located within said sense elements such that said pathways provide individual electrical interconnection to said probe elements and cooperate as transmission lines; and
   a substantially lossless, structurally supporting connector means operatively connected to said sense elements which cooperate to electrically interconnect said conductive pathways to external electronic devices.

2. Apparatus in accordance with claim 1 wherein said flexible structure is fabricated using a photo-lithographic process to alternately dispose patterns onto at least one layer of a dielectric material.

3. Apparatus in accordance with claim 1 further including means for aligning and registering said flexible structure including a slideably mounted mechanical scanning apparatus.

4. Apparatus in accordance with claim 2 wherein fabrication is accomplished by High Density Interconnect processing to accommodate computerized control of said patterns.

5. Apparatus in accordance with claim 2 wherein said at least one drive element is disposed onto at lest one layer.

6. Apparatus in accordance with claim 5 wherein each of said sense elements is comprised of at least one coil winding deposited onto said at least one layer.

7. Apparatus in accordance with claim 6 wherein said sense elements are selectively comprised of a plurality of electrically interconnected coil windings.

8. Apparatus in accordance with claim 7 wherein at lest one of said sense elements is comprised of at lest two coil windings electrically interconnected in a differential mode.

9. Apparatus in accordance with claim 7 wherein at least one of said sense elements is comprised of at least two coil windings electrically interconnected in an absolute mode.

10. Apparatus in accordance with claim 3 wherein said scanning apparatus slideably scans said inspection surface in a predetermined direction such that said sense elements are organized into a plurality of parallel rows disposed substantially normal to said predetermined scanning direction with at least one row of said parallel rows staggered with respect to at least one other row.

11. Apparatus in accordance with claim 7 wherein select conductive pathways electrically interconnecting select individual drive elements cooperate as transmission lines.

12. Apparatus in accordance with claim 11 wherein select conductive pathways electrically interconnecting select individual sense elements cooperate as transmission lines.

13. Apparatus in accordance with claim 12 wherein conductive shielding strips are selectively disposed between select said conductive pathways.

14. Apparatus in accordance with claim 1 wherein said conductive pathways terminate on either surface of said dielectric structure and are organized into respective terminal leads.

15. Apparatus in accordance with claim 14 wherein said connector means further comprises a substantially rigid, nonconductive connector module integral with said dielectrical structure and including conductive finger-like strips disposed thereon such that said strip electrically interconnect with said terminal leads.

16. Apparatus in accordance with claim 15 wherein said connector module is operatively inserted into an edge connector having a plurality of miniature contact strips for making respective electrical interconnection with said finger-like strips such that said edge connector provides electrical interconnection to said external electronic device.

17. Apparatus in accordance with claim 15 wherein an elastomeric connector having a plurality of conductive matrix elements disposed throughout an insulating, surface pressure deformable substrate and extending substantially therethrough, is disposed between said finger-like strips of said connector module and corresponding electrical conduct surfaces of said external electronic device to make electrical interconnection therebetween.

18. Apparatus in accordance with claim 17 wherein said connector means further includes mechanical coupling means integral to said connector module to operatively couple with corresponding mechanical coupling means integral to said external electronic device.

19. Apparatus in accordance with claim 18 wherein said mechanical coupling means includes at least one insertion opening and at least one correspondingly disposed insertion pin.

20. Apparatus in accordance with claim 14 wherein said connector means comprises said flexible eddy current probe array structure having said terminal leads organized as exposed surface contact leads, said structure being laminated onto a substantially rigid, nonconductive substrate in order to form an insertion edge having said surface contact leads exposed for insertion into an edge connector, said edge connector having a plurality of corresponding electrical contact surfaces in order to make electrical interconnection therewith.

21. Apparatus in accordance with claim 20 wherein said array structure is laminated onto a surface of said substrate in order to accommodate single-sided electrical interconnection.

22. Apparatus in accordance with claim 20 wherein said array structure is laminated onto both surfaces of said substrate in order to accommodate double-sided electrical interconnection.

23. Apparatus in accordance with claim 14 wherein said terminal leads are organized as a plurality of contact pads disposed on an exposed surface of said probe array structure after lamination onto a substantially rigid, nonconductive substrate wherein selectively aligned contact pads are brought into electrical interconnection with respective contact surfaces of said external electronic device by electrically coupling through an elastomeric connector disposed therebetween, said connector provides a plurality of conductive matrix elements disposed throughout an insulating, surface pressure deformable substrate, wherein said matrix elements provide direct, electrical interconnection therebetween.

24. Apparatus in accordance with claim 23 wherein means for selective alignment includes at least one structurally integral registration and coupling means aligned with respect to said contact pads in order to correspondingly couple with at least one similarly disposed coupling means on said external electronic device.

25. Apparatus according to claim 3 wherein said array is outwardly affixed onto a substantially rigid, nonconductive supporting surface such that said supporting surface is the mated complement of said inspection surface.

26. Apparatus according to claim 3 wherein clamping means are an integral part of said eddy current probe array structure.

27. Apparatus according to claim 26 wherein said clamping means includes at lest one structurally integral coupling means designed to couple with a mounting apparatus such that said mounting apparatus includes at least one corresponding coupling means for clamping thereto, said mounting apparatus operating to actuate said supporting surface for scanning of said inspection surface.

28. Apparatus according to claim 26 wherein said clamping means includes at least one coupling means aligned to couple with said rigid supporting surface such that said supporting surface includes at least one corresponding coupling means for precisely positioning said probe array structure with respect to said inspection surface.

* * * * *